United States Patent [19]

Bright

[11] Patent Number: 4,851,388

[45] Date of Patent: Jul. 25, 1989

[54] HEPTANOYL-GLU-ASP-ALA-AMINO ACID IMMUNOSTIMULANTS

[75] Inventor: Gene M. Bright, Groton, Conn.

[73] Assignee: Pfizer Inc., New York, N.Y.

[21] Appl. No.: 137,534

[22] PCT Filed: Jan. 23, 1986

[86] PCT No.: PCT/US86/00126

§ 371 Date: Aug. 17, 1987

§ 102(e) Date: Aug. 17, 1987

[87] PCT Pub. No.: WO87/04440

PCT Pub. Date: Jul. 30, 1987

[51] Int. Cl.$^4$ .................. A61K 37/02; C07K 5/08
[52] U.S. Cl. .................................... 514/18; 530/331
[58] Field of Search ..................... 514/18; 530/331

[56] References Cited

U.S. PATENT DOCUMENTS 4,354,966 10/1982 Kitaura .
4,394,308 7/1983 Sampathkumar .
4,399,066 8/1983 Nakaguchi .

OTHER PUBLICATIONS

Chem. Pharm. Bull. 17, 1679–1686 (1969), "Peptides. I. Selective Protection of Alpha- or Side-Chain Carboxyl Groups of Aspartic and Glutamic Acid."
Kitaura, J. Med. Chem. 25,335–337 (1982).

Primary Examiner—Delbert R. Phillips
Attorney, Agent, or Firm—Peter C. Richardson; Albert E. Frost; Lawrence C. Akers

[57] ABSTRACT

Peptides useful as antiinfective agents, immunomodulators for stimulation of host defenses in patients with an increased risk of bacterial infections, intermediates and process therefor.

14 Claims, No Drawings

HEPTANOYL-GLU-ASP-ALA-AMINO ACID IMMUNOSTIMULANTS

BACKGROUND OF THE INVENTION

1. Field of the Invention

This invention relates to certain novel acyltripeptides useful as antiinfective agents and immunomodulators for stimulation of host defenses in patients with an increased risk of bacterial infection, to intermediates therefor and to a process for making said acyltripeptides.

2. Description of the Prior Art

The relatively new field of immunopharmacology, and particularly that segment thereof which deals with immunomodulation, continues to develop at a rapid pace. A variety of naturally occurring compounds has been investigated, including the tetrapeptide tuftsin, known chemically as $N^2$-[1-($N^2$-L-threonyl-L-lysyl)-L-prolyl]-L-arginine. Much attention has been directed to synthetic peptidoglycan derivatives, especially those known as muramyl dipeptides. For summaries of the wide range of compounds investigated as immunomodulators, and especially as immunostimulants, attention is directed to Dukar et al., Annu. Rep. Med. Chem., 14, 146–167 (1979), Lederer, J. Med. Chem., 23, 819–825 (1980) and to J. Kralovec, *Drugs of the Future*, 8, 615–638 (1983).

Immunostimulant peptides have been described in a number of patent specifications:

L-Alanyl-alpha-glutaric acid N-acyl dipeptides in German Pat. No. 3,024,355, published Jan. 15, 1981;

tetra- and penta-peptides containing D-alanyl-L-glutamyl moieties or L-alanyl-D-glutamyl moieties in Brit. Pat. No. 2,053,231, published Feb. 4, 1981 and German Pat. No. 3,024,281, published Jan. 8, 1981, respectively; and N-acyl-L-alanyl-alpha-D-glutamyl tripeptide derivatives in which the C-terminal amino acid is lysine or diaminopimelic acid in Ger. Pat. No. 3,024,369, published Jan. 15, 1981; and lactyl tetrapeptides composed of N-lactylalanyl, glutamyl, diaminopimelyl and carboxymethylamino components in EP-11283, published May 28, 1980.

Further immunostimulant polypeptides having the formula (A)

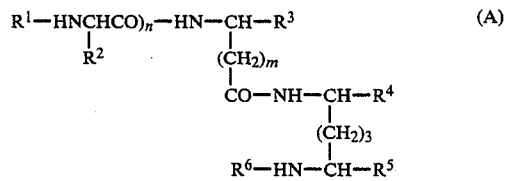

wherein $R^1$ is hydrogen or acyl; $R^2$ is inter alia hydrogen, lower alkyl, hydroxymethyl, benzyl; $R^3$ and $R^4$ are each hydrogen, carboxy, —$CONR^7R^8$ wherein $R^7$ is hydrogen, lower alkyl optionally substituted with hydroxy; and $R^8$ is mono- or dicarboxy lower alkyl; $R^5$ is hydrogen or carboxy with the proviso that when one of $R^4$ and $R^5$ is hydrogen, the other is carboxy or —$CONR^7R^8$; $R^6$ is hydrogen; m is 1 to 3 and n is 0 to 2, and derivatives thereof in which the carboxy and amino groups are protected are disclosed in U.S. Pat. Nos. 4,311,640 and 4,322,341; EP applications Nos. 25,482; 50,856; 51,812; 53,388; 55,846 and 57,419.

Kitaura et al., J. Med. Chem., 25, 335–337 (1982) report $N^2$-(gamma-D-glutamyl)-meso-2(L),2'(D)-diaminopinemic acid as the minimal structure capable of eliciting a biological response characteristic of the compound of formula (A) wherein n is 1; $R^1$ is $CH_3CH(OH)$—CO—; $R^2$ is $CH_3$; each of $R^3$ and $R^5$ is —COOH; $R^4$ is —$CONHCH_2COOH$; and $R^6$ is H. Said compound of formula (A) is known as FK-156.

SUMMARY OF THE INVENTION

It has now been found that compounds of formula (I) wherein each of Y, Z, $R^1$ and $R^2$ is hydrogen are efficient immunomodulators.

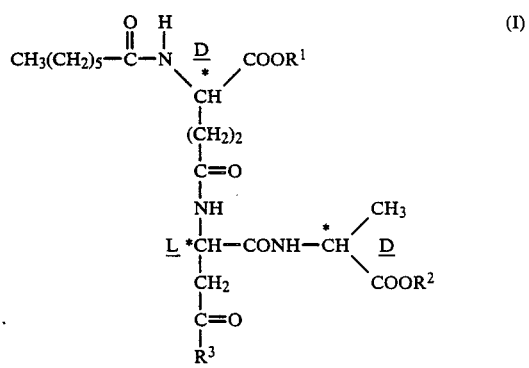

wherein $R^1$ is hydrogen or benzyl; $R^2$ is hydrogen or methyl; $R^3$ is

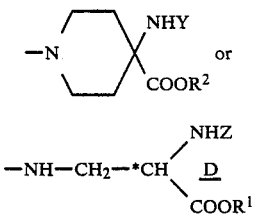

wherein Z is hydrogen; and Y is hydrogen and pharmaceutically acceptable salts of those compounds wherein at least one of Y, Z, $R^1$ or $R^2$ is hydrogen. Formula (I) compounds wherein at least one of Y, Z, $R^1$ and $R^2$ is other than hydrogen are intermediates for those compounds wherein Y, Z, $R^1$ and $R^2$ are hydrogen.

Also included in this invention are certain other compounds useful as intermediates for production of compounds of formula (I). The intermediates have formulae (II) and (III):

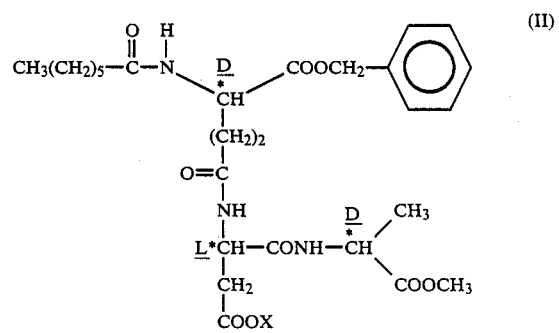

wherein X is hydrogen or tert-butyl; and

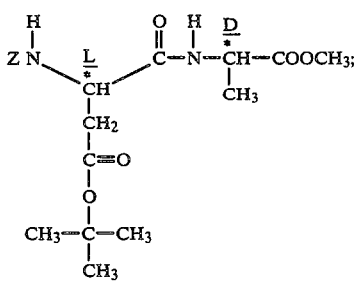

(III)

wherein Z is hydrogen or carbobenzyloxy.

The configuration of the amino acid moieties which make up the formula (I) compounds is significant as regards the pharmacological activity of said compounds. The most potent activity is observed in formula (I) compounds having the stereochemistry indicated in said formula. The stereochemistry, relative to that of the natural amino acid, is designated as D- or L-.

Also included in this invention are pharmaceutically acceptable salts, especially the alkali metal, and the sodium and potassium salts in particular, of formula (I) compounds. Such salts are readily prepared by reacting the acid forms of formula (I) compounds ($R^1$, $R^2$, Y and Z=H) with a stoichrometric amount of the appropriate alkali metal hydroxide in aqueous acetone. Removal of the solvent affords the desired salt.

Compounds of formula (I) are prepared by the reaction sequence shown below. The methodology involves the formation of peptide linkages between amino acids which, because of their amino and carboxy groups, necessitate the protection of said groups and/or the activation of such groups, particularly the carboxy group, in order to achieve a certain reaction or to optimize such a reaction. The overall sequence is unique as regards the protecting groups used in the various steps. The different protecting groups employed are necessary for successful and optimal outcome of the sequence since they allow convenient and selective removal of a given group at a certain step with retention of a protecting group or groups at other sites. Since three different protecting groups, each of which is removable under a specific set of reaction conditions is used, the reaction sequence is described as being triorthogonal. It is this triorthogonality which renders the present process unique.

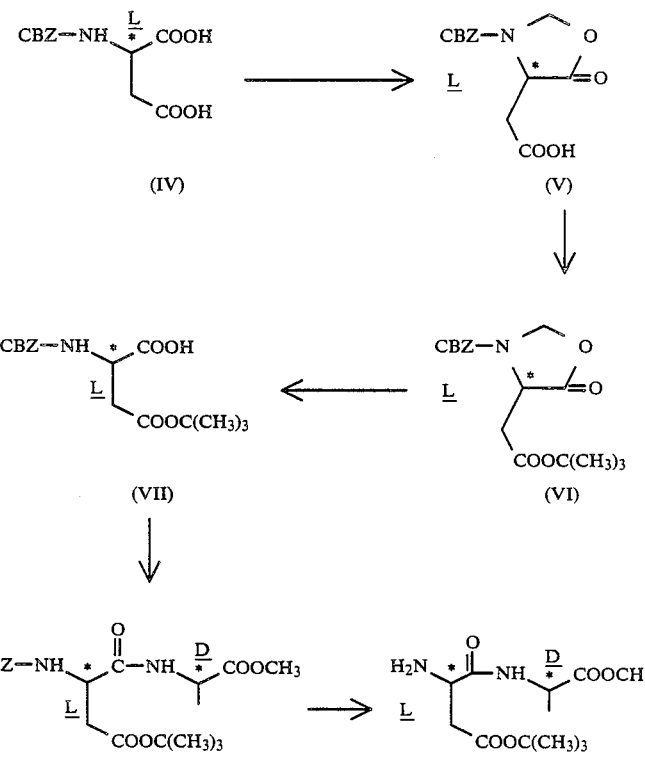

-continued

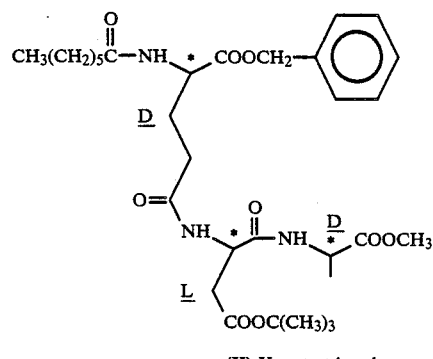

(II) X = tert-butyl

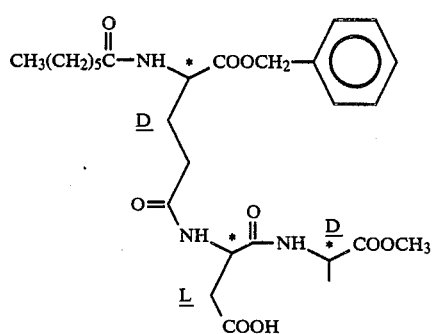

(II) X = H (I)

Each of the three protecting groups, the tert-butyl on the beta carboxy group of the aspartic acid moiety, the methyl on the carboxy group of the alanine moiety, and the benzyl on the carboxy group of the glutamic acid moiety is important to preparation of formula (I) compounds wherein each of $R^1$ and $R^2$ is hydrogen and $R^3$ is as defined above. Selective removal of each of said protecting groups allows one to perform reactions at a desired site without affecting other sites. For example, removal of the tert-butyl group from the protected aspartic acid moiety enables one to introduce groups $R^3$ at said site to produce formula (I) compounds.

Compounds (IV), (V), (VI) and (VII) are known compounds described by Itoh. Chem. Pharm. Bull. 17, 1679–1686 (1969). Compound (VII), beta-tert-butyl N-benzyloxycarbonyl-L-aspartate, also known as carbobenzyloxy-L-aspartic acid beta tert-butyl ester is also described by Schroder et al. Ann. Chem. 673, 208 (1964). Conversion of (VII) to (III), carbobenzyloxy-alpha-L-aspartyl-D-alanine methyl ester beta tert-butyl ester, is accomplished by acylation of (VII) with D-alanine methyl ester hydrochloride in a reaction inert solvent; i.e., one which does not react appreciably with reactants or products, in the presence of a coupling agent, preferably a carbodiimide. The choice of carbodiimide reagent used is of no importance even though certain of them, e.g., $N,N^1$-dicyclohexylcarbodiimide, tend to give rise to racemization. The racemization can be minimized by the presence in the reaction mixture of 1-hydroxybenzotriazole (1-2 equivalents) or substituted derivatives thereof, or N-hydroxy succinimide (1-2 equivalents) which form active esters and serve to expedite the reaction. In the present invention 1-cyclohexyl-3-(2-morpholinoethyl)carbodiimide metho-p-toluene sulfonate is a favored coupling agent.

Suitable solvents for this coupling reaction are methylene chloride, ether, benzene, dioxane and N,N-dimethylformamide.

An acid acceptor is also used in the reaction to liberate the free amino-ester product (III). The preferred base is N-methylmorpholine although other bases, e.g., pyridine, triethylamine as long as they do not cause undersirable side reactions such as hydrolysis of the ester reactants and products, can be used.

This coupling reaction is conveniently carried out by adding all reactants in the order illustrated in Example 1; i.e., reactant (III), 1-hydroxybenzotriazole, acid acceptor, reactant to be coupled to (III) and the coupling agent. Each reactant is allowed to dissolve before adding the next reactant to afford a smooth reaction. The reaction is run at a temperature of from about $-10°$ C. to about $+10°$ C. during this addition step, again for smoothness of reaction, and then allowed to warm to ambient temperature to complete the reaction. Higher temperatures up to the boiling point of the solvent can be used, if desired.

The compound of formula (III) wherein Z is carbobenzyloxy is next converted to the compound of formula (III) wherein Z is hydrogen by catalytic hydrogenolysis according to procedures known to those skilled in the art. The favored procedure of this invention comprises hydrogenation using palladium hydroxide on carbon (and especially Pearlman's catalyst: palladium hydroxide content 20%, water content 31%) at a hydrogen pressure of from about 1 to about 100 psi (from 0.07 to 7.03 kg/sq. cm) and preferably at about 50 psi (3.52 kg/sq. cm) in methanol. The product is recovered by standard procedures.

The next step in the sequence introduction of the heptanoyl glutamyl moiety; i.e., conversion of (III) wherein Z is hydrogen to (II), is accomplished by an acylation reaction as described above for conversion of (VII) to (III).

The formula (II) compound thus obtained wherein X is tert-butyl is then transformed by anhydrous acid in an inert solvent to the formula (II) compound wherein X is hydrogen. The hydrolysis is carried out in an appropriate solvent, such as anhydrous acid-dioxane or anhydrous acid-tetrahydrofuran, at ambient temperature. The favored acids are mineral acids such as HCl, HBr, HF and $HNO_3$. The preferred acid is anhydrous HCl. The product is recovered by known procedures, e.g., by removal of solvent and extraction of the residue.

Introduction of the $R^3$ groups into the formula (II) compound wherein X is hydrogen is achieved by the acylation procedure described above for preparation of (III) from (VII).

It will be noted that the amino groups of the amino acids which serve as reactants for $R^3$ groups; namely,

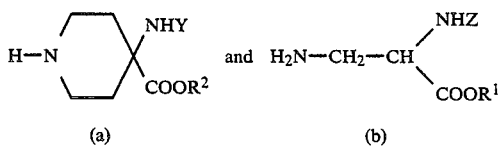

are protected by appropriate groups. In reactant (a), Y represents the tert-butyloxycarbonyl group; and in (b), Z represents the carbobenzyloxy group. The carboxy groups of (a) and (b) are protected as the methyl and benzyl esters, respectively. However, the nature of the protecting groups in (a) or (b) is not relevant to the overall sequence. Said protecting groups afforded convenient syntheses of (a) and (b). Other protecting groups can be used.

The products of this invention are useful as immunomodulators for stimulating host (mammal) defenses versus a bacterial challenge. They are of particular value to animals, especially humans, having an increased risk of bacterial infection due to existing or clinically-induced immunosuppression. They are used in conjunction with antibacterial agents which are effective against the particular bacterial challenge.

The test procedure, which uses $C_3H/HeN$ male mice from the Charles River Breeding Laboratory, is presented below. The mice were acclimatized for 5 days before use and then treated either subcutaneously (SC) or orally (PO) with various dilutions (10, 1 and 0.1 mg/kg) of the test compound or placebo (pyrogen free saline) using a volume of 0.2 ml. The treatment regimen was dependent on the infectious organism utilized: −24 and 0 hours before challenge for *Klebsiella pneumoniae*; said challenge being administered intramuscularly (IM) in the hip. A volume of 0.2 ml was used for the challenge. Mortality was recorded after 7 days. Culture Preparation;

*K. pneumoniae*: the culture was streaked for purity from frozen blood stock on brain heart infusion (BHI) agar. Three colonies were picked from the 18 hour plate culture and placed into 9 ml of BHI broth. The broth culture was grown for 2 hours at 37° C. on a rotary shaker after which 0.2 ml was streaked on the surface of several BHI agar slants. Following an 18 hour incubation at 37° C., the slants were washed with BHI broth, the culture density adjusted using a spectronic 20 and the appropriate dilution made to achieve an LD100 challenge level in mice (approx. 250 CFU/animal). (CFU = Colony forming units).

When used as immunomodulators as immunostimulant agents in humans, the compounds of this invention are conveniently administered via the oral, subcutaneous, intramuscular, intravenous or intraperitoneal routes, generally in composition form. Such compositions include a pharmaceutical practice. For example, they can be administered in the form of tablets, pills, powders or granules containing such excipients as starch, milk sugar, certain types of clay, etc. They can be administered in capsules, in admixtures with the same or equivalent excipients. They can also be administered in the form of oral suspensions, solutions, emulsions, syrups and elixirs which may contain flavoring and coloring agents. For oral administration of the therapeutic agents of this invention, tablets or capsules containing from about 50 to about 500 mg are suitable for most applications.

The physician will determine the dosage which will be most suitable for an individual patient and it will vary with the age, weight and response of the particular patient and the route of administration. Generally, however, the initial dosage in adults may range from about 2–100 mg/kg per day in single or divided doses. The favored oral dosage range is from about 10 to about 300 mg/kg/day. The favored parenteral dose is from about 0.1 to about 100 mg/kg/day; the preferred range from about 0.1 to about 20 mg/kg/day.

This invention also provided pharmaceutical compositions, including unit dosage forms, valuable for the use of the herein described compounds for the utilities disclosed herein. The dosage form can be given in single or multiple doses, as previously noted, to achieve the daily dosage effective for a particular utility.

The following examples are provided solely for the purpose of further illustration. In the interest of brevity, the following abbreviations for peak shapes in the NMR spectra are used: s, singlet; d, doublet; t, triplet; q, quartet; m, multiplet.

EXAMPLE 1

Carbobenzyloxy-alpha-(L)-aspartyl-D-alanine methyl ester-beta-tert-butyl ester

To a well-stirred solution of 78.2 g (0.24 moles) of carbobenzyloxy-L-aspartic acid-beta-tert-butyl ester [Itoh, Chem. Pharm. Bull. 17, 1679–1686 (1969)] in 3 liters of anhydrous methylene chloride at 0°–5° C. under a nitrogen atmosphere, 32.62 g (0.24 moles of 1-hydroxybenzotriazole, 23.0 ml (21.16 g, 0.21 moles) of N-methylmorpholine, 28.10 g (0.20 moles) of D-alanine methyl ester hydrochloride, and 107.28 g (0.25 moles) of 1-cyclohexyl-3-(2-morpholinoethyl) carbodiimide metho-p-toluene sulfonate were successively added, each reagent being dissolved before adding the next. The reaction mixture was then stirred at ambient temperature for 18 hours and then sequentially washed with 2.5 liter portions of 5% aqueous hydrochloric acid, water, saturated aqueous sodium bicarbonate, and finally water. The sodium sulfate-dried organic phase was concentrated in vacuo to afford the crude product (84.5 g) as a light yellow syrup. A portion of the crude product (30.0 g) was chromatographed on a flask column using 1500 g of silica gel (fine mesh) and eluting with ethyl acetate/hexane = gel 1:1.5. Progress of the column was followed by thin-layer chromatography (silica gel tlc plates; elution with ethyl acetate/hexane=1:1; development with heat and 10% ethanolic spray; product $R_f$=0.41). Column fractions containing only pure product were combined and concentrated in vacuo to afford the title compound as a colorless solid, 10.95 g (37% yield). $^{13}$Cnmr (CDCl$_3$) ppm 172.9, 170.6, 170.1 (amide, ester carbonyls), 156.1 (carbamate carbonyl), 136.2, 128.5, 128.2, 128.1 (aromatic carbons), 81.7, 67.2, 52.3, 51.4, 48.2, 37.5, 28.0, 18.0; $^1$Hnmr (CDCl$_3$) delta 1:37 (3H, d, alanyl CH$_3$—), ABX pattern with H$_A$ and H$_B$ multiplets (2H, aspartyl methylene protons) centered at 2.62 and 2.90, H$_X$ within unresolved multiplet 4.5–4.63 (2H, aspartyl and alanyl methine protons); 3.72 (3H, s, —CO$_2$CH$_3$); 5.14 (2H, m, benzylic protons), 7.35 (5H, m, aromatic protons).

Scale up of the above procedure using 145 g (0.449 mole) of carbobenzyloxy-L-aspartic acid-beta-tert-butyl ester, 60.7 g. (0.449 mole) of 1-hydroxybenzotriazole, 41.0 ml (37.72 g, 0.374 mole) of N-methylmorpholine, 52.19 g (0.374 mole) of D-alanine methyl ester hydrochloride, and 200 g (0.449 mole) of 1-cyclohexyl-3-(2-morpholinoethyl) carbodiimide metho-p-toluene sulfonate afforded 160.9 g of crude product (yellow syrup). The entire crude product was taken up in 1.5 liters of methylene chloride and silica gel (170 g of 32–63 mesh) was added. The mixture was shaken vigorously and dried in vacuo. The silica gel absorbed crude product was loaded onto a chromatography column loaded with 1 kg of silica gel in ethyl acetate/hexane (1:2). Elution with ethyl acetate/hexane (1:2) (tlc monitoring of column fractions) afforded 140.2 g (92% yield) of the pure title product as a waxy solid.

EXAMPLE 2

Alpha-(L)-aspartyl-D-alanine methyl ester-beta-tert-butyl ester

A solution of 62.5 g (0.153 mmoles) of carbobenzyloxy-alpha-(L)-aspartyl-D-alanine methyl ester-beta-tert-butyl ester in 950 ml of anhydrous methanol was hydrogenated at 50 psi at 20° C. on a Parr apparatus for 5 hours using 63 g of palladium hydroxide on carbon catalyst (Pearlman's catalyst: palladium hydroxide content 20%, water content 31%). The reaction mixture was filtered and the filter cake subsequently washed with two 500 ml portions of methanol. The filtrate and methanol washings were combined and concentrated in vacuo to an oil. The crude product was dissolved in one liter of ethyl acetate, and the resulting solution was sequentially washed with 500 ml of 5% aqueous sodium bicarbonate and 500 ml of water, then dried over sodium sulfate. The dried organic phase was then concentrated in vacuo to afford the title compound as a colorless oil (29.6 g, 70% yield). $^1$Hnmr (60 mHz, CDCl$_3$), delta 1.39 (3H, d, J=7Hz), 1.45 (9H, s), 2.3–2.8 (2H, m), 3.5–3.8 (1H, partially obscured m), 3.72 (3H, s), 4.52 (1H, m), 7.75 (broad, d).

EXAMPLE 3

Heptanoyl-gamma-D-glutamyl-alpha-benzyl ester-alpha-(L)-aspartyl-alpha-D-alanine methyl ester-beta-tert-butyl ester Heptanoyl-gamma-D-glutamic alpha-benzyl ester (13.91 g, 39.8 mmoles), alpha-(L)-aspartyl-D-alanine methyl ester-beta-tert-butyl ester (9.10 g, 33.0 mmoles), 1-hydroxybenzotriazole (5.38 g, 39.8 mmoles), and 1-cyclohexyl-3-(2-morpholinoethyl) carbodiimide metho-p-toluene sulfonate (17.75 g, 39.8 mmoles) were combined in that order in 396 ml of anhydrous methylene chloride at 0°–5° C. The mixture was then stirred at 20° C. for 20 hours. After dilution with 300 ml of methylene chloride, the reaction mixture was washed with one liter each of 5% aqueous hydrochloric acid, saturated aqueous sodium bicarbonate, and water. The organic phase was dried over sodium sulfate and concentrated in vacuo to an oil. The crude product (21.7 g) was chromatographed on 1700 g of silica gel (32–63 mesh), eluting with ethyl acetate/hexane=3:1. Column fractions containing the desired product as determined by thin-layer chromatography (silica gel tlc plates; elution with ethyl acetate/hexane=3:1; development with heat and 10% ethanolic phosphomolybdic acid spray) were combined and the solvent was removed in vacuo, affording a colorless solid residue. The residue was dissolved in 400 ml of ethyl acetate and washed twice with 400 ml of 1N aqueous sodium hydroxide, and then with 400 ml of water (to remove a trace impurity). Concentration of sodium sulfate-dried organic phase afforded the pure title compound as an amorphous colorless solid (6.27 g, 31% yield). $R_f$=0.68 (silica gel tlc plates, elution with ethyl acetate/hexane=1:1; developed with heat and 10% ethanolic phosphomolybdic acid spray). $^{13}$Cnmr (CDCl$_3$) ppm 173.4, 172.9, 172.1, 172.0, 170.8, 170.2 (carbonyls); 135.3, 128.6, 128.4, 128.3 (aromatic carbons); 67.2, 81.6, 52.2, 51.5, 49.4, 48.3 (—CO$_2$CH$_3$ and amino acid asymmetric carbons); 36.9, 36.4, 32.0, 31.5, 28.9, 28.0, 25.5, 22.4, 17.6, 14.0. $^1$Hnmr (CDCl$_3$) multiplets at delta 0.83 and 1.1–1.7 [H, CH$_3$(CH$_2$)$_4$— and glutamyl C-3 methylene protons], 1.34 (3H, d, J=7Hz, alanine CH$_3$—); 1.40 [9H, s, —C(CH$_3$)$_3$], overlapping multiplets 2.1–2.4 (4H, heptanoyl C-2 and glutamyl C-4 methylene protons); ABX pattern with H$_A$ multiplet centered at 2.57 (1H), H$_B$ multiplet centered at 2.78 (1H), H$_X$ multiplet centered at 4.47 (1H), J$_{AB}$=15Hz, J$_{AX}$≈J$_{BX}$=6Hz, aspartyl methylene and methine protons; 7.30 (5H, m, aromatic protons).

EXAMPLE 4

Heptoanoyl-gamma-D-glutamyl-alpha-benzyl ester-alpha-L-aspartyl-D-alanine methyl ester Heptanoyl-gamma-D-glutamyl-alpha-benzyl ester-alpha-(L)-aspartyl-D-alanine methyl ester-beta-tert-butyl ester [6.13 g (10.0 mmoles)] was dissolved in 10.1 ml of anhydrous 5N hydrochloric acid-dioxane solution, and stirred at ambient temperature for 1.5 hours. The solvent was removed in vacuo, the residue taken up in 300 ml of ethyl acetate, and the resulting solution washed with 350 ml of saturated aqueous sodium bicarbonate. The separated aqueous phase was layered with 450 ml of fresh ethyl acetate while the pH was adjusted to 1.5 by addition of 6N aqueous hydrochloric acid (considerable frothing). After good mixing, the phases were separated, and the aqueous phase was extracted twice more with 350 ml portions of ethyl acetate. The combined ethyl acetate extracts were washed with 600 ml of water, dried over sodium sulfate, and concentrated in vacuo to afford the title compound as a colorless foam: 4.52 g (82%) yield. $R_f=0.23$ (silica gel tlc plates, elution with acetic acid/ethyl acetate/n-butanol/water=1:1:1:1; plate developed with heat and 10% ethanolic phosphomolybdic acid spray). $^{13}$Cnmr (CD$_3$OH) ppm 176.3, 174.7, 174.4, 173.8, 173.1, 172.7, 53.2, 52.8, 51.1. $^1$Hnmr (CD$_3$OD) multiplets at delta 0.9 and 1.2–1.7 [13H, CH$_3$(CH$_2$)$_4$— and glutamyl C-3 methylene protons], 1.37 (3H, d, J=7Hz, alanine CH$_3$—); two multiplets 2.2–2.4 (4H, heptanoyl C-2 and glutamyl C-4 methylene protons); ABX pattern with H$_A$ multiplet centered at 2.65 (1H), H$_B$ multiplet centered at 2.84 (1H), H$_X$ multiplet centered at 4.80, $J_{AB}$=18Hz, $J_{AZ} \approx J_{BX}$=6Hz, aspartyl methylene and methine protons; 3.68 (3H, s, —CO$_2$CH$_3$); two overlapping multiplets 4.36–4.53 (2H), glutamyl and alanyl methine protons.

EXAMPLE 5

Benzyl N$^3$-[Heptanoyl-gamma-D-glutanyl-alpha-benzyl ester-beta-(L)-aspartyl-alpha-D-alanine methyl ester]-N$^2$-carbobenzyloxy-D-2,3-diaminopropionate To an ice-bath chilled solution of 3.78 g (0.0138 moles) of N$^2$-carbobenzyloxyl-D-2,3-diaminopropionate monohydrochloride in 795 ml of anhydrous methylene chloride, 5.43 g (9.88 moles) of heptanoyl-gamma-D-glutamyl-alpha-benzyl ester-alpha-(L)-aspartyl-D-alanine methyl ester, 1.80 ml (16.4 moles) of N-methyl morpholine, 1.45 g (10.7 moles of 1-hydroxybenzotriazole, and 3.84 g (9.1 moles) of of 1-cyclohexyl-3-(2-morpholinoethyl)-carbodiimide metho-p-toluenesulfonate were added in that order. The cooling bath was removed, and the reaction mixture was stirred for 17 hours at ambient temperature. The organic layer was then washed twice with one liter of 1N aqueous hydrochloric acid. The organic and aqueous layers emulsified during the acid wash. The emulsion was broken by a final washing of the emulsified portion with one liter of water. The organic layer was then washed twice with one liter of 1N aqueous sodium hydroxide. Again, after removal of the clear aqueous phase, the emulsified portion was cleared by a one liter water wash. The organic phase was dried over magnesium sulfate, rotoevaporated, and then dried in vacuo to afford the title compound as a colorless granular solid, 5.78 g (74% yield). $^1$Hnmr (CD$_3$OD) multiplets at delta 0.9 and 1.2–1.7 [13H, CH$_3$(CH$_2$)$_4$— and glutamyl C-3 methylene]; 1.35 (3H, d, alanine CH$_3$—); 3.67 (3H, s, —CO$_2$CH$_3$); 4.3–4.5 (4H, overlapping multiplets,

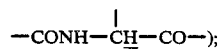

multiplets at 5.1 (2H) and 5.17 (4H), benzylic —CH$_2$—; 7.34 (15H, m, aromatic protons).

EXAMPLE 6

N$^3$-[Heptanoyl-gamma-D-glutamyl-beta-(L)-aspartyl-alpha-D-alanine methyl ester]-D-2,3-diaminopropionic acid A solution of 0.83 g (0.97 mmoles) of benzyl N$^3$-[heptanoyl-gamma-D-glutamyl-alpha-benzyl ester-beta-(L)-aspartyl-alpha-D-alanine methyl ester]-N$^2$-carbobenzyloxy-D-2,3-diaminopropionate in 280 ml of ethanol was hydrogenated using 1.3 g of Pearlman's Catalyst (palladium hydroxide on carbon; palladium hydroxide content 20%, water content ca. 31%) on a Parr Apparatus at 50 psi for 55 hours. The catalyst was filtered and the solvent was removed in vacuo to afford 374 mg (71% yield) of the title compound as a colorless amorphous solid. $R_f$=0.49 (silica gel tlc plate; elution with acetic acid/ethyl acetate/water/n-butanol=1:1:1:1; plate developed with heat and 10% ethanolic phosphomolybdic acid spray). $^1$Hnmr (DMSO-d$_6$) delta 0.86 (3H, m) and 1.05–1.86 (16H, overlapping series of multiplets; CH$_3$(CH$_2$)$_4$—, glutamyl C-3 methylene protons, alanine—CH$_3$); 2.06–2.33 (4H, m, heptanoyl C-2 and glutamyl C-4 methylene protons); 2.35–2.67 (2H, m, aspartyl methylene protons), 3.1–3.8 (2H, broad m; methylene protons, diaminopropionic acid moiety), 3.62 (3H, s, —CO$_2$CH$_3$); two overlapping multiplets 4.06–4.35 (2H) and 4.5 (1H, m), amino acid methine protons.

EXAMPLE 7

N$^3$-[Heptanoyl-gamma-D-glutamyl-beta-(L)-aspartyl-alpha-D-alanine]-D-2,3-diaminopropionic acid, trisodium salt To an ice-bath cooled solution of 2.00 g (3.7 mmoles) of N$^3$-[heptanoyl-gamma-D-glutamyl-beta-(L)-aspartyl-alpha-D-alanine methyl ester]-D-2,3-diaminopropionic acid in 8.3 ml of water and 25 ml of acetone, 10.923 ml (10.9 mmoles) of 1.00N sodium hydroxide was added all at once. The ice-bath was removed, and the solution was stirred for 1.5 hours at ambient temperature. Rotoevaporation of acetone and lyophilization afforded the title compound as an amorphous colorless solid, 2.14 g (97% yield); $R_f$=0.46 (silica gel tlc plate; elution with acetic acid/ethyl acetate/n-butanol/water=1:1:1:1; plate developed with heat and 10% ethanolic phosphomolybdic acid spray). $^{13}$Cnmr (D$_2$O) ppm 180.6, 179.8, 178.5, 176.8, 175.8, 172.3, 171.8, 55.98, 54.95, 51.42, 51.16.

EXAMPLE 8

N$^3$-[Heptanoyl-gamma-D-glutamyl-alpha-benzyl ester-beta-(L)-aspartyl-alpha-D-alanine methyl ester-4-(tert-butyloxycarbonyl amino)-4-carbomethoxy-piperidine To an ice-bath chilled solution of 1.00 g (3.87 mmole) of 4-tert-butyloxycarbonylamino)-4-carboxymethoxy-piperidine in 300 ml of anhydrous methylene chloride, 1.90 g (3.46 mmole) of heptanoyl-gamma-D-glutamyl-alpha-benzyl ester-alpha-(L)-aspartyl-D-alanine methyl ester, 0.52 g (3.58 mmole) of 1-hydroxybenzotriazole, and 1.44 g (4.06 mmole) of 1-cyclohexyl-3-(2-morpholinoethyl)carbodiimide metho-p-toluenesulfonate were added in that order. The reaction was stirred 18 hours at ambient temperature. The mixture was washed twice with equal volumes of aqueous 1N sodium hydroxide, and once with equal volumes of 1N aqueous hydrochloric acid, water, and finally brine. The separated organic phase was dried over anhydrous sodium sulfate and concentrated in vacuo to a colorless solid (1.94 g). This crude product was combined with 93 mg of crude product obtained in a pilot run (1/20 scale) carried out in identical fashion. The combined crudes were chromatographed on a 150 g silica gel (32–62 mesh) column, eluting with ethyl acetate/methanol=98:2 and following progress of the column by thin-layer chromatography (product $R_f$=0.24; silica gel tlc plate; elution with ehtyl acetate/methano/=9.8:0.2; developed with heat and 10% ethanolic phosphomolybdic acid spray). Thus 1.04 g of the pure title compound (36% yield) was isolated as a colorless amorphous solid. $^1$Hnmr (60 mHz, CDCl$_3$), delta 1.45 (9H, s), two overlapping singlets at 3.71, 3.72 (6H), 5.14 (2H, s), 7.31 (5H, s).

EXAMPLE 9

N$^3$-[Heptanoyl-gamma-D-glutamyl-alpha-benzyl ester-beta-(L)-aspartyl-alpha-D-alanine methyl ester]-4-amino-4-carbomethoxy-piperidine N$^3$-[Heptanoyl-gamma-D-glutamyl-alpha-benzyl ester-beta-(L)-aspartyl-alpha-alanine methyl ester]-4-(tert-butyloxycarbonyl amino)-4-carbomethoxy-piperidine (1.04 g, 1.31 mmoles) was stirred in 6.8 ml of a 4N anhydrous hydrochloric acid solution in dioxane (20° C.) for 4 hours. The reaction was concentrated in vacuo to an oil which was dissolved in 60 ml of ethyl acetate. The solution was stirred with 80 ml of water; and the pH was adjusted to 2.0 with aqueous 2N hydrochloric acid. The well-mixed phases were separated (following addition of sufficient brine to clear an emulsion), and the aqueous phase was extracted with an equal volume of fresh ethyl acetate. Both ethyl acetate extracts were discarded. The aqueous phase was then stirred with 80 ml of fresh ethyl acetate, and the pH was adjusted to 9.5 with 2N aqueous sodium hydroxide. The separated aqueous phase was extracted with a second fresh portion of ethyl acetate. The two ethyl acetate extracts of the basic aqueous phase were combined, washed with an equal volume of water, sodium sulfate dried, and concentrated in vacuo to afford the title compound as a colorless foam, 564 mg (63% yield). The product, shown to be essentially pure by thin-layer chromatography. ($R_f$=0.50; silica gel tlc plates; elution with acetic acid/n-butanol/water=1/4/1; developed with heat and 10% ethanolic phosphomolybdic acid spray), was used in the next step without further purification.

EXAMPLE 10

N$^3$-[Heptanoyl-gamma-D-glutamyl-beta-(L)-aspartyl-alpha-alanine methyl ester]-4-amino-4-carbomethoxypiperidine A solution of 564 mg (0.82 mmoles) of N$^3$-[heptanoyl-gamma-D-glutamyl-alpha-benzyl ester-beta-(L)-aspartyl-alpha-alanine methyl ester]-4-amino-4-carbomethoxypiperidine in 106 ml of methanol was hydrogenated at 50 psi (20° C.) on a Parr apparatus for 18 hours, using 395 mg of Pearlman's catalyst (palladium hydroxide on carbon; palladium hydroxide content 20%, water content 31%). The catalyst was filtered and washed with 150 ml of hot methanol. The methanol washing and filtrate were combined and concentrated in vacuo to afford the title compound as a colorless foam, 478 mg (98% yield). $R_f$=0.36 (silica gel plate; elution with acetic acid/n-butanol/water=1:4:1; development with heat and 10% ethanolic phosmolybdic acid spray). $^1$Hnmr (60 mHz, CD$_3$OD, delta 3.73 (3H, s) and 3.86 (3H, s), —CO$_2$CH$_3$.

EXAMPLE 11

N$^3$-[Heptanoyl-gamma-D-glutamyl-beta-(L)-aspartyl-alpha-D-alanine]-4-amino-4-carboxy-piperidine, trisodium salt To a 5° C. solution of 100 mg (0.17 mmoles) of N$^3$-[heptanoyl-gamma-D-glutamyl-beta-(L)-aspartyl-alpha-alanine methyl ester]-4-amino-carbomethoxy-piperidine in 1.3 ml of acetone and 0.4 ml of water, 0.491 ml of 1.000N aqueous sodium hydroxide (0.49 mmoles) was added all at once. The solution was stirred at 5° C. for 3 hours. Lyophilization of the resulting clear solution afforded the title compound (97 mg, 92% yield) as a colorless amorphous solid. $R_f$=0.26 [silica gel tlc plate; elution with acetic acid/n-butanol/water=1:4:1; plate developed with heat and 10% ethanolic phosphomolybdic acid spray]. $^{13}$Cnmr (D$_2$O) ppm 183.4, 179.9, 178.6, 176.9, 175.8, 171.9, 169.9, 56.8, 55.0, 51.5, 51.0, 43.2, 39.5, 36.3, 35.5, 35.0, 32.7, 31.1, 28.4, 25.6, 22.2, 18.2, 13.8.

PREPARATION A

N-Carbobenzyloxy-4-amino-4-carboxy-piperidine 4-amino-4-carboxy-piperidine hydrobromide ([P. Jacobsen, K. Schaumburg, P. Krogsgaard-Larsen, *Acta. Chem.* Scandinavica B34, 319–326 (1980)]; 2.25 g, 10 mmoles) was dissolved in a solution of 18 ml potassium dihydrogen phosphate buffer (0.05 Molar potassium dihydrogen phosphate in 1N aqueous sodium hydroxide) and 6 ml of water. The solution was chilled with an ice-bath over an hour period during which solutions of carbobenzyloxy chloride (1.57 ml, 11 mmoles) in 3.0 ml of toluene and aqueous 1N sodium hydroxide were simultaneously added dropwise so as to maintain a pH of 7.0. The mixture was then stirred for one hour at 5° C., and for four additional hours at ambient temperature. The precipitate formed during the reaction was filtered and the filter cake washed with 3 (30 ml) portions of diethyl ether. The amorphous colorless solid was dried in vacuo affording 1.4 g of the title compound (50% yield). $^1$Hnmr (60 mHz; CF$_3$CO$_2$D) delta 2.0–2.7 (4H, broad m), 3.5–4.5 (4H, broad m), 5.28 (2H, s), 7.4 (5H, s).

PREPARATION B

N-Carbobenzyloxy-4-amino-4-carbomethoxy-piperidine

Distilled thionyl chloride (1.25 ml; 2.05 g; 17.2 mmoles) was added to 19.0 ml of anhydrous methanol. N-carbobenzyloxy-4-amino-4-carboxy-piperidine (0.5 g; 1.8 mmoles) was dissolved in one-third (6.6 ml) of the thionylchloride/methanol mixture, and the resulting solution refluxed for 20 minutes. Another third (6.6 ml) of the thionyl chloride/methanol reagent was added to the reaction which was then refluxed for one hour. The final third portion (6.6 ml) of thionyl chloride/methanol reagent was added to the reaction followed by another one hour reflux. The reaction mixture was then concentrated in vacuo to 5 ml volume; and 40 ml of ethyl acetate was added. A precipitate (hydrochloride salt of unreacted starting material; 120 mg) was filtered off, and the mother liquor concentrated in vacuo to afford a white solid (347 mg). The crude product was dissolved in 25 ml of chloroform and stirred with 25 ml of water, the pH of the aqueous phase being adjusted to 8.4 by addition of saturated aqueous sodium bicarbonate. The aqueous layer was separated and extracted with an equal volume of chloroform. The combined chloroform extracts were dried (sodium sulfate) and concentrated in vacuo to afford the desired product as a colorless oil (228 mg, 43% yield). $R_f=0.51$ (silica gel plate; elution with methylene chloride/methanol=9:1; development with heat and 10% ethanolic phosphomolybdic acid spray). $^1$Hnmr (60 mHz, CDCl$_3$) delta 1.2–2.3 (6H, m), 3.2–4.0 (4H, m), 3.72 (3H, s), 5.16 (2H, s), 7.39 (5H, s).

PREPARATION C

N-Carbobenzyloxy-4-(tert-butyloxycarbonylamino)-4-carbomethoxy-piperidine

To a solution of 1.958 g (6.7 mmoles) N-carbobenzyloxy-4-amino-4-carbomethoxy-piperazine in 1.0 ml of dry methylene chloride, 1.60 g (7.36 mmoles) of di-tert-butyl dicarbonate (Aldrich Chemical Co.; Milwaukee, Wisconsin) was added; and the tightly stoppered solution was stirred at ambient temperature for 48 hours. After removal of solvent in vacuo, the residue was combined with the crude residue of a previous analogously conducted (0.12 scale) pilot reaction, and dissolved in 20 ml of methylene chloride. The solution was then washed with equal volumes of cold 1N aqueous hydrochloride acid, water and saturated aqueous sodium bicarbonate. The organic phase was dried over anhydrous magnesium sulfate, filtered, and concentrated in vacuo to an oil (2.47 g). The oil was triturated with 80 ml of hexane for 15 minutes. The hexane was then carefully decanted. The trituration procedure was repeated six times causing the oil to solidify, thus affording the title compound as a colorless amorphous solid which was dried in vacuo; 1.07 g (36% yield). $R_f=0.6$ (silica gel plate; elution with methylene chloride/methanol=9:1; developed with heat and 10% ethanolic phosphomolybdic acid spray). $^1$Hnmr (60 mHz, CDCl$_3$) delta 1.49 (9H, s), 1.8–2.2 (4H, m), 2.9–4.05 (4H, very broad multiplet). 3.67 (3H, s), 5.07 (2H, s), 7.24 (5H, s).

PREPARATION D 4-(tert-butyloxycarbonylamino)-4-carbomethoxy-piperidine

A solution of 1.56 g (4.0 mmoles) of N-carbobenzyloxy-4-(tert-butyloxycarbonylamino)-4-carbomethoxy-piperidine in 150 ml of methanol was hydrogenated at 50 psi (20° C.) on a Parr apparatus for 18 hours, using 1.01 g of Pearlman's catalyst (palladium hydroxide on carbon; palladium hydroxide content 20%, water content 31%). The catalyst was filtered and the filtrate concentrated in vacuo to afford the title compound (1.02 g; 100% yield) as a colorless amorphous solid. $^1$Hnmr (60 mHz, CDCl$_3$) delta 1.23 (9H, s), 1.8–2.35 (4H, broad m), 2.78–3.23 (4H, broad m), 3.77 (3H, s).

I claim:

1. A compound of the formula

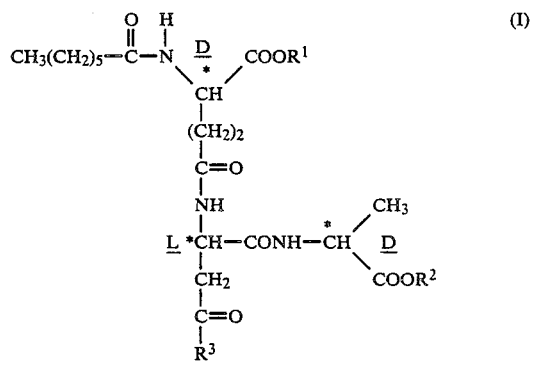

wherein

R$^1$ is hydrogen or benzyl;

R$^2$ is hydrogen or methyl;

R$^3$ is

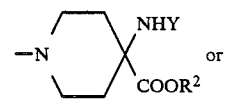

or

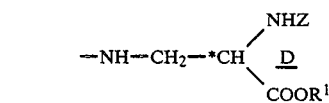

wherein Z is hydrogen or carbobenzyloxy; and Y is hydrogen or t-butoxycarbonyl, and pharmaceutically acceptable salts of those compounds wherein at least one of Y, Z, R$^1$ or R$^2$ is hydrogen.

2. A compound according to claim 1 wherein R$^3$ is

3. A compound according to claim 2 wherein each of Y and R$^1$ is hydrogen.

4. The compound according to claim 3 wherein R$^2$ is hydrogen.

5. A compound according to claim 1 wherein R$^3$ is

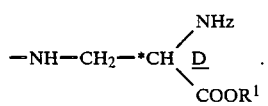

6. A compound according to claim 5 wherein each of R$^1$ and Z is hydrogen.

7. The compound according to claim 5 wherein R$^2$ is hydrogen.

8. A compound of the formula

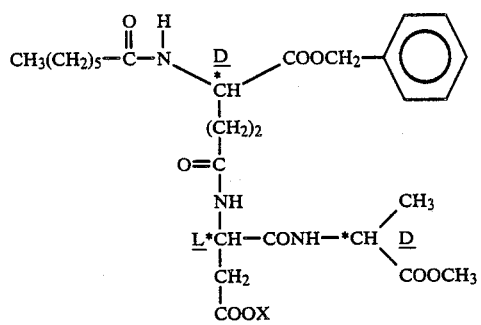 (II)

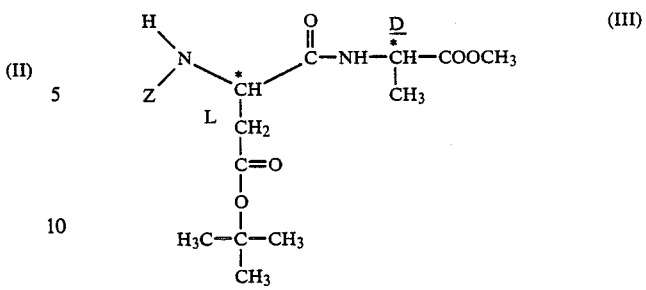 (III)

wherein X is hydrogen or t-butyl.

9. The compound according to claim 8 wherein X is hydrogen.

10. The compound according to claim 8 wherein X is t-butyl.

11. A compound of the formula wherein Z is hydrogen or benzyloxycarbonyl.

12. The compound of claim 11 wherein Z is hydrogen.

13. A method of treating an infection in a mammal suffering therefrom which comprises administering to said mammal an antiinfective effective amount of a compound of claim 1 wherein each of $R^1$, $R^2$, Y and Z is hydrogen, or a pharmaceutically acceptable salt thereof.

14. A pharmaceutical composition comprising a pharmaceutically acceptable carrier and an immunostimulant effective amount of a compound of claim 1 wherein each of $R^1$, $R^2$, Y and Z is hydrogen, or a pharmaceutically acceptable salt thereof.

* * * * *